(12) United States Patent
Cooper et al.

(10) Patent No.: US 7,297,211 B2
(45) Date of Patent: Nov. 20, 2007

(54) SINGLE-DOSE SPRAY SYSTEM FOR APPLICATION OF LIQUIDS ONTO THE HUMAN BODY

(75) Inventors: Steven C. Cooper, Athens, GA (US); Troy H. Cooper, Addison, TX (US); Ricky C. Croft, Dallas, TX (US)

(73) Assignee: Mystic Tan, Inc., Farmers Branch, TX (US)

( * ) Notice: Subject to any disclaimer, the term of this patent is extended or adjusted under 35 U.S.C. 154(b) by 0 days.

(21) Appl. No.: 10/841,734

(22) Filed: May 7, 2004

(65) Prior Publication Data

US 2005/0039678 A1 Feb. 24, 2005

Related U.S. Application Data

(60) Provisional application No. 60/469,289, filed on May 9, 2003.

(51) Int. Cl.
   *B05C 11/10* (2006.01)
(52) U.S. Cl. .................. 118/684; 118/695; 118/696; 118/685; 118/681
(58) Field of Classification Search ............... 118/695, 118/696, 679, 680, 681, 684, 685, 320, 323; 604/289, 290, 296
See application file for complete search history.

(56) References Cited

U.S. PATENT DOCUMENTS 1,982,509 A * 11/1934 Frank .......................... 604/289

| | | | |
|---|---|---|---|
| 2,954,146 A * | 9/1960 | Hullman | ..................... 222/630 |
| 4,004,733 A | 1/1977 | Law | |
| 4,289,276 A | 9/1981 | Bollina et al. | |
| 4,343,433 A | 8/1982 | Sickles | |

(Continued)

FOREIGN PATENT DOCUMENTS

EP 0 031 649 A2 7/1981

(Continued)

OTHER PUBLICATIONS

Cooper, S. C. and Law, S. E., "Electrostatic Sprays for Sunless Tanning of the Human Body", Proceedings of the ESA-IEEE Joint Meeting on Electrostatics, Jun. 25, 2003, pp. 1-12, University of Arkansas, Little Rock, Arkansas.

*Primary Examiner*—George Koch
(74) *Attorney, Agent, or Firm*—Gardere Wynne Sewell LLP

(57) ABSTRACT

A spray device for coating a surface of a human body with a spray liquid, the spray device including at least one nozzle and at least one liquid container, wherein the at least one liquid container adapted to hold a volume of spray liquid substantially equal to an amount required to apply a single dosage of the spray liquid for coating a surface of a human body. The spray device further includes a liquid channel adapted to connect the at least one liquid container to the at least one nozzle, and a spray valve adapted to cause the spray liquid to flow from the at least one liquid container to the at least one nozzle using the liquid channel, the at least one nozzle producing a spray jet of the spray liquid. The spray device still further includes a control device adapted to control the operation of the spray device, and a sweeping device for sweeping the spray jet from the at least one nozzle to coat at least a portion of the human body.

60 Claims, 9 Drawing Sheets

U.S. PATENT DOCUMENTS

| | | | |
|---|---|---|---|
| 4,357,900 A | 11/1982 | Buschor | |
| 4,664,315 A | 5/1987 | Parmentar et al. | |
| 4,688,518 A | 8/1987 | Missier | |
| 4,731,058 A | 3/1988 | Doan | |
| 4,846,525 A | 7/1989 | Manning | |
| 4,941,808 A | 7/1990 | Qureshi et al. | |
| 5,101,679 A | 4/1992 | Smith et al. | |
| 5,163,010 A * | 11/1992 | Klein et al. | 700/239 |
| 5,268,166 A | 12/1993 | Barnett et al. | |
| 5,277,713 A | 1/1994 | Gelain et al. | |
| 5,322,684 A | 6/1994 | Barnett et al. | |
| 5,387,200 A | 2/1995 | Kronstadt | |
| 5,460,192 A | 10/1995 | McClain | |
| 5,494,674 A | 2/1996 | Barnett et al. | |
| 5,527,564 A | 6/1996 | Napadow et al. | |
| 5,545,140 A | 8/1996 | Conero et al. | |
| 5,664,593 A | 9/1997 | McClain | |
| 5,704,554 A | 1/1998 | Cooper et al. | |
| 5,738,728 A | 4/1998 | Tisone | |
| 5,765,761 A | 6/1998 | Law et al. | |
| 5,833,751 A | 11/1998 | Tucker | |
| 5,863,497 A | 1/1999 | Dirksing | |
| 5,922,333 A | 7/1999 | Laughlin | |
| 6,003,794 A | 12/1999 | Hartman et al. | |
| 6,138,922 A | 10/2000 | Hartman et al. | |
| 6,199,557 B1 | 3/2001 | Laughlin | |
| 6,227,466 B1 | 5/2001 | Hartman et al. | |
| 6,302,122 B1 | 10/2001 | Parker et al. | |
| 6,302,662 B1 | 10/2001 | Bensley et al. | |
| 6,326,062 B1 | 12/2001 | Noakes et al. | |
| 6,387,081 B1 | 5/2002 | Cooper | |
| 6,443,164 B1 | 9/2002 | Parker et al. | |
| 6,554,208 B1 | 4/2003 | Venuto, Sr. | |
| 6,802,830 B1 | 10/2004 | Waters et al. | |
| 2003/0127542 A1 | 7/2003 | Cooper | |
| 2004/0073186 A1* | 4/2004 | Cameron | 604/389 |

FOREIGN PATENT DOCUMENTS

| | | |
|---|---|---|
| EP | 0 031 649 B1 | 9/1984 |
| EP | 0 224 352 B1 | 8/1990 |
| EP | 0 441 501 A1 | 8/1991 |
| EP | 0 468 736 A1 | 1/1992 |
| EP | 0 468 736 B1 | 3/1997 |
| EP | 0 441 501 B1 | 8/1997 |

* cited by examiner

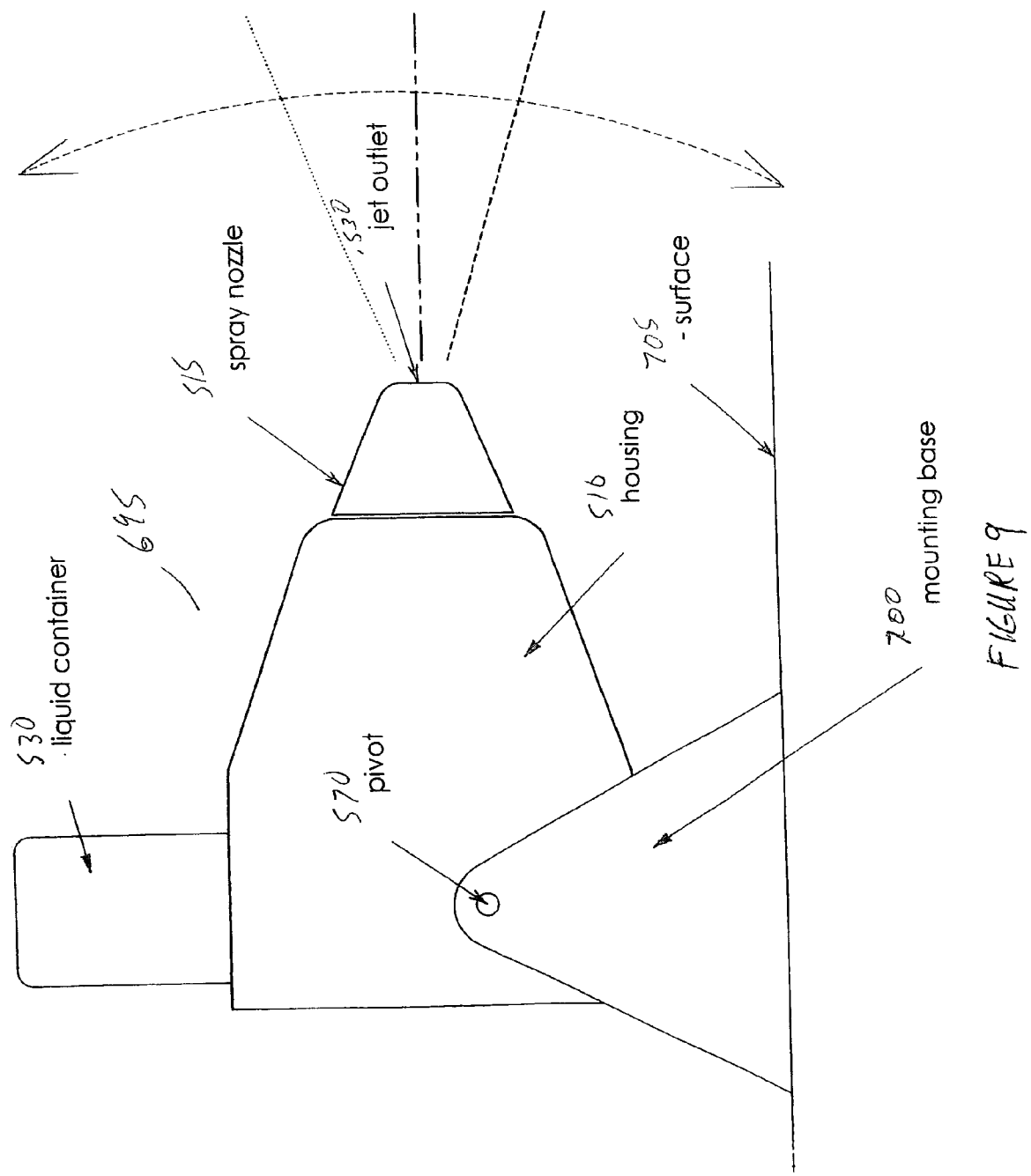

SINGLE-DOSE SPRAY SYSTEM FOR APPLICATION OF LIQUIDS ONTO THE HUMAN BODY

CROSS-REFERENCE TO RELATED APPLICATIONS

This application claims the benefits of and priority to U.S. Provisional Patent Application No. 60/469,289 filed May 9, 2003, the disclosure of which is incorporated by reference.

BACKGROUND OF THE INVENTION

Spray devices for the application of liquids onto human skin and hair are well known. Spray applications are used for many types of medicines, hair treatments, deodorants, lotions, and cosmetic agents. One form of spray device for the application of liquids for skin treatment are hand-held spray devices. Usually these hand-held spray devices are comprised of disposable pressurized can spray applicators having a finger actuated spray valve and nozzle. Non-pressurized hand-held spray applicators are also available consisting of reusable trigger-pump spray devices. These disposable and refillable trigger sprayers are held in one hand at less than a meter away from the skin to treat portions of the body. Container sizes for these types of sprayers are adapted to hold volumes of liquids adequate for multiple applications from a single container. Uniform spray applications of a precise dosage or coverage of an entire body are difficult with these types of hand-held spray applicators.

Other types of hand held applicators are those with liquid containers that use liquid pressure or compressed gas for atomization and propulsion. An example of this type of hand-held applicator is a hand-held air-brush sprayer adapted to be used to dispense cosmetic agents. One disadvantage of such air-brush systems is that the liquid containers are of an inappropriate size, often being too large or too small, to coat an entire person or selected parts of a person. In addition, the refilling process for such devices can be messy.

Another disadvantage of hand-held air-brush systems is that it is difficult for a person to self-apply an even coat to certain body portions, such as the back. To overcome this problem, professional salons and spas offer trained sunless-tanning applicator personnel to apply material carefully over the entire body of the customer. This situation is often inconvenient and uncomfortable for both the personnel and the customer. In addition, since hand-held airbrush applications usually take 10 to 30 minutes, the process can be irritating to the tanning applicator and the customer due to prolonged exposure to the spray environment. Fatigue is also known to occur in the back, arms, and wrists of applicator personnel due to the repetitive motion of the hand-held brushing process.

Applications of cosmetic agents, such as sunless tanning compounds, with hand-held spray devices require very experienced personnel to avoid mistakes which may result in under- or over-application, missed areas, streaks, and runs. Another drawback that limits the practicality and marketplace potential of hand-held cosmetic sprays in which an assistant is needed is the potential inconvenience and embarrassment to the person being coated, since they must stand for the duration of the application in an unclothed or partially unclothed state.

Non-hand-held systems for dispensing liquid to the human body have also been developed. U.S. Pat. No. 1,982,509 describes a prior system for applying treatment media to a living body. U.S. Pat. No. 1,982,509 describes a carrier device which moves up and down and provides for applying a treatment media to a body. However, U.S. Pat. No. 1,982,509 does not describe for the use of removable liquid containers, or for liquid containers adapted to be of a size for applying a single dosage to portions of a human body as provided by embodiments of the present invention.

Automated systems for self-application of a spray mist to the entire body have recently been introduced for sunless tanning. These systems are housed within cabinets or booths to permit enclosure of an adult and provide for hands-free, uniform, self-application in a private setting. U.S. Pat. No. 5,922,333 to Laughlin, U.S. Pat. No. 6,387,081 to Cooper, U.S. Pat. No. 6,302,122 to Parker et al., and U.S. Pat. No. 6,443,164 to Parker et al. each describe automated systems for coating the human body in which a spray chamber is used. In present systems, several spray nozzles are fed from a single large tank containing sunless tanning solution. These automatic spray systems are designed to dispense approximately five to ten tanning sessions per liter of liquid, and generally use a feeder-tank capacity of eight to twenty liters. Since each customer's dose is drawn from a common tank, the customer has no assurance of the amount applied, nor do they have a choice of the type of lotion to be applied for a certain skin type or desired tanning color. It is not currently practical to adapt present automatic systems to dispense a single dosage from an individually sized container because of the wasted volume of spray liquid that resides in the many hoses that are required to feed each of the many spray nozzles. The various embodiments of the present invention provide for a self-application spray device having a liquid container closely connected to a nozzle system and of a size allowing a customer to dispense an appropriate volume of spray solution of their choice.

BRIEF SUMMARY OF THE INVENTION

One embodiment of the present invention is directed to a spray device including at least one nozzle and at least one liquid container, the at least one liquid container adapted to hold a volume of spray liquid substantially equal to an amount required to apply a single dosage of the spray liquid for coating the surface of a human body. The spray device further includes a liquid channel adapted to connect the at least one liquid container to the at least one nozzle, and a spray valve adapted to cause the spray liquid to flow from the at least one liquid container to the at least one nozzle using the liquid channel, the at least one nozzle producing a spray jet of the spray liquid. The spray device still further includes a control device adapted to control the operation of the spray device, and sweeping means for sweeping the spray jet from the at least one nozzle to coat at least a portion of the human body.

Another embodiment of the present invention is directed to a spray device for coating the surface of a human body with a spray liquid. The spray device includes at least one nozzle, and at least one liquid container, the at least one liquid container adapted to hold a volume of spray liquid of less than one liter. The spray device further includes a liquid channel adapted to connect the at least one container to the at least one nozzle, a spray valve adapted to cause the spray liquid to flow from the at least one container to the at least one nozzle using the liquid channel, the at least one nozzle producing a spray jet of the spray liquid. The spray device further includes a control device adapted to control the operation of the spray device, and sweeping means for sweeping the spray jet from the at least one nozzle to coat at least a portion of the human body.

Another embodiment of the present invention is directed to a spray device including at least one nozzle, and at least one removable liquid container, the at least one removable liquid container adapted to hold a volume of spray liquid substantially equal to an amount required to apply a single dosage of the spray liquid for coating the surface of a human body. The spray device further includes a receiver adapted to receive the at least one removable liquid container, and a liquid channel adapted to connect the at least one removable liquid container to the at least one nozzle. The spray device further includes a spray valve adapted to cause the spray liquid to flow from the at least one removable liquid container to the at least one nozzle using the liquid channel, the at least one nozzle producing a spray jet of the spray liquid, a control device adapted to control the operation of the spray device, mounting means for mounting the spray device to a surface, and sweeping means for sweeping the spray jet from the at least one nozzle to coat at least a portion of the human body.

Another embodiment of the present invention is directed to a spray device including at least one nozzle, and at least one liquid container, the at least one liquid container adapted to hold a volume of spray liquid substantially equal to an amount required to apply a single dosage of the spray liquid for coating the surface of a human body. The spray device further includes a liquid channel adapted to connect the at least one liquid container to the at least one nozzle, and a pressurized gas conduit, the pressurized gas conduit adapted to connect a source of compressed gas to the at least one nozzle. The spray device further includes a spray valve adapted to cause pressurized gas to flow from the source of pressurized gas to the at least one nozzle using the gas conduit, wherein the flow of pressurized gas to the at least one nozzle facilitates flow of the spray liquid from the at least one liquid container to the at least one nozzle using the liquid channel, the at least one nozzle producing a spray jet of the spray liquid. The spray device still further includes a control device adapted to control the operation of the spray device, and sweeping means for sweeping the spray jet from the at least one nozzle to coat at least a portion of the human body.

Still another embodiment of the present invention is directed to a spray device including at least one nozzle, at least one liquid container, a liquid channel adapted to connect the at least one liquid container to the at least one nozzle, and a spray valve adapted to cause the spray liquid to flow from the at least one liquid container to the at least one nozzle using the liquid channel, the at least one nozzle producing a spray jet of the spray liquid. The spray device further includes a control device adapted to control the operation of the spray device, and positioning means for manually positioning the spray jet from the at least one nozzle to coat at least a portion of a human body.

BRIEF DESCRIPTION OF THE DRAWINGS

FIG. 9 illustrates another embodiment of a mounting arrangement for use with at least one embodiment of the spray device of the present invention.

DETAILED DESCRIPTION OF THE INVENTION

Figure 1:
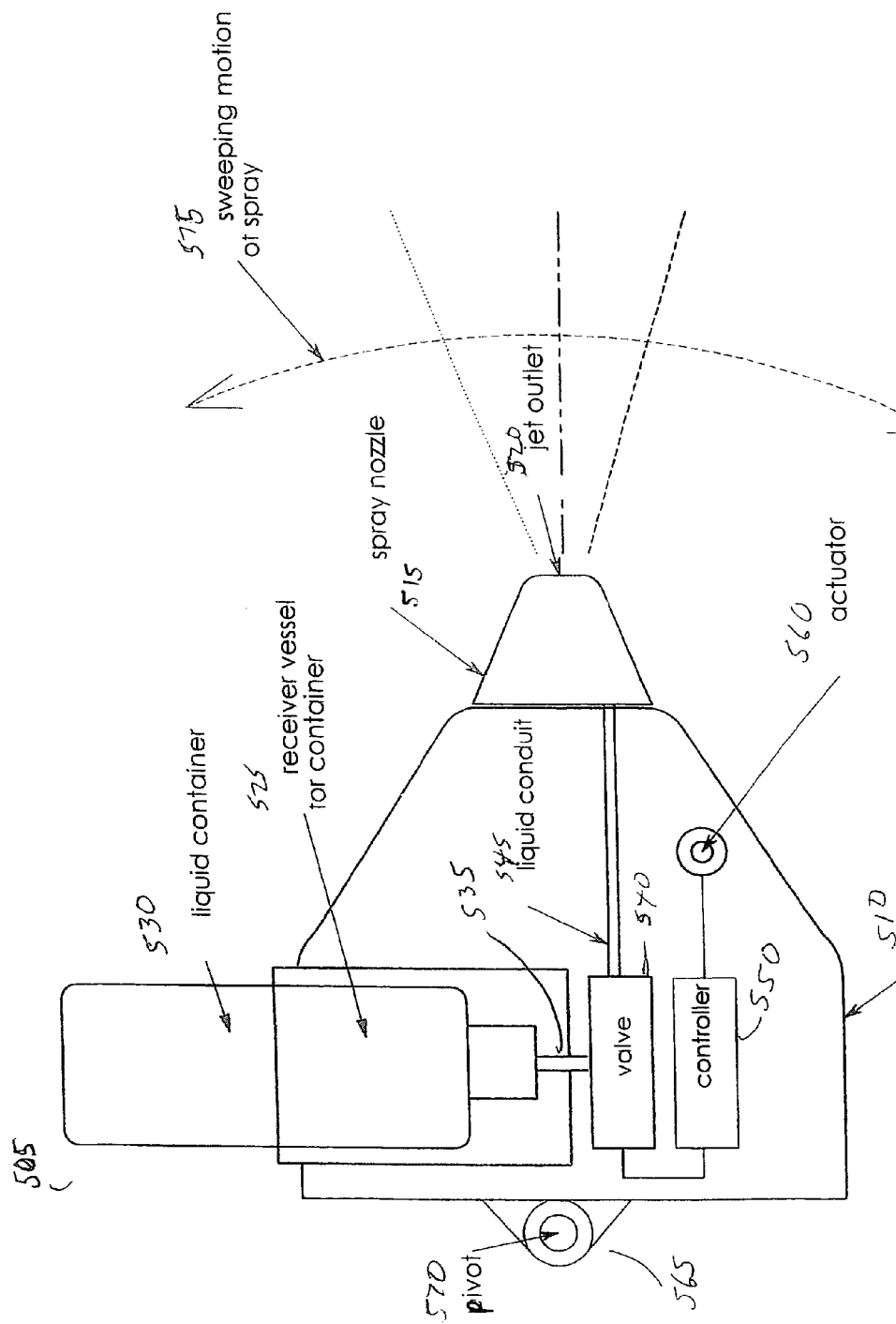
FIG. 1 illustrates a spray device adapted to coat a surface of a human body with a spray liquid in accordance with an embodiment of the present invention.

Referring now to FIG. 1, a spray device adapted to coat a surface of a human body with a spray liquid, such as a sunless tanning compound, in accordance with an embodiment of the present invention is illustrated. The spray device 505 includes a housing 510 having an attached spray nozzle 515. The spray nozzle 515 includes a jet outlet 520 for dispensing a spray of liquid to cover a portion of a human body. In another embodiment of the present invention, the spray nozzle 515 may be comprised of an electrostatic spray nozzle adapted to produce electrostatically charged droplets of the spray liquid. Many types of electrostatic spray nozzles exist in the prior art, of which many are suitable for use in embodiments of the present invention.

The housing 510 contains a receiver vessel 525 adapted to receive and support an inserted removable liquid container 530. In accordance with an embodiment of the present invention, the removable liquid container 530 is adapted to be disposable or refillable after use. In accordance with one embodiment of the present invention, the receiver vessel 525 may be of a shape so that it mates with the outside shape of the removable liquid container 530 to properly orient the removable liquid container 530 within the receiver vessel 525, as well as ensure that the correct container is used in the spray device 505. Upon insertion of the removable liquid container 530 into the receiver vessel 525, a receiver conduit 535 connected to a liquid valve 540 punctures a liquid seal in the removable liquid container 530. In accordance with an embodiment of the present invention, the removable liquid container 530 is adapted to be of a size to contain an amount of liquid substantially equal to that required to apply a single dosage of the liquid to be sprayed to coat a surface of a human body. For example, this volume may be in the range of 100 ml to 150 ml. The amount of liquid substantially equal to that required to apply a single dosage may vary in accordance with the type of liquid and efficiency of the spray device, for example, between a range of 100 ml to 500 ml. In accordance with another embodiment of the present invention, the removable liquid container 530 may be adapted to hold a volume of spray liquid of less than one liter. In accordance with still another embodiment of the present invention, the removable liquid container 530 may comprise a disposable liquid container or a refillable liquid container.

Upon opening of the liquid valve 540, the liquid in the removable liquid container 530 is allowed to flow through a liquid conduit 545, or a liquid channel, to the spray nozzle 515, and exit the spray nozzle through jet outlet 520 in the form of a liquid spray. The removable liquid container 530 may optionally be pressurized or vented to facilitate the dispensing of liquid from the liquid container 530. In addition, the receiver vessel 525 may be provided with a vent. In accordance with an embodiment of the present embodiment, the spray device 505 further includes a controller 550 connected to the liquid valve 540. In an embodiment of the present invention, the liquid conduit 545 is adapted to be of a length such that the distance that the liquid is required to flow between the liquid valve 540 and the spray nozzle 515 is short. In accordance with an embodiment of the present invention, the length of the liquid conduit 545 is less than approximately 160 millimeters. In accordance with another embodiment of the present invention, the liquid conduit 545 is adapted to hold less than 20 ml of liquid. At least one advantage provided by the liquid conduit 545 being of a relatively short length and small diameter is that during a single tanning session, sequential use of multiple removable liquid containers can be used without requiring the purging of the liquid conduit 545. For example, a particular customer may desire to have a pre-tanning compound from a first removable liquid container be applied, and then subsequently have a tanning compound from a second removable liquid container be applied. In accordance with other embodiments of the present invention, the liquid conduit 545 may be adapted to be contained within the liquid valve 540, the spray nozzle 515, or a fitting.

The controller 550 functions as a control device to control operation of the liquid valve 540. An actuator 560 is further connected to the controller 550 to allow an operator to control operation of the controller 550. In accordance with various embodiments, the actuator 560 may be comprised of an electrical switch, a hand-held actuator or remote control, mounted on the housing 510 of the spray device 505, or mounted on a wall or a floor near the person to be coated by the liquid spray, thereby providing remote activation of the spray device 505 by hand or foot while allowing a person to be coated to stand at an optimum distance away from the spray nozzle 515. The remote activation provided by the actuator 560 allows, for example, for a person being coated to move body parts or completely turn in order to achieve uniform coverage. It should be understood that activation of the spray device 505 may be controlled either by an operator or the person to be coated. In accordance with other embodiments of the present invention, the controller 550 may comprise a timer circuit to control spray duration, or a programmable controller to provide for a variable spray duration. In other embodiments of the present invention other means of initiating a control sequence may be used, such as sensing the insertion of the liquid container into the spray device.

In accordance with still other embodiments of the present invention, the actuator 560 can be adapted to control the valve 540 via a wireless connection, such as an infrared or other light signal, a radio signal, a motion signal, or a voice activation or another sound signal. The actuator 560 can optionally be provided with an electrical connection to connect an operator to earth ground. In still other embodiments, the actuator 560 may comprise a hydraulic flow device or a pneumatic flow device connected to the spray device 505 via a tube.

In accordance with the present embodiment, the spray device 505 further includes a sweeping means 565 that is adapted to oscillate the spray device 505 about a pivot point 570 in a sweeping motion 575, such as in a predetermined arc, while spraying. The sweeping motion 575 imparted to the spray nozzle 515 provides for the liquid spray from the nozzle jet outlet 520 to provide a larger area of coverage than that provided by a stationary nozzle. The sweeping means 565 may be comprised of, for example, an oscillating motor, one or more solenoids, or hydraulic actuators.

In accordance with an embodiment of the spray device 505 of FIG. 1, the controller 550 is further adapted to control the sweeping motion of the spray device 505. For example, in addition to starting and stopping the spray jet from the spray jet outlet 520, the controller 550 may be used to start and stop the sweeping movement, control the speed of the sweeping movement, and/or control the range of the sweeping movement of the spray device 505. Activation of the controller 550 to start the sweeping movement of the spray device 505 can be initiated through use of the actuator 560 and/or automatically by the controller 550. Similarly, stopping of the sweeping movement of the spray device 505 can be initiated through use of the actuator 560 and/or automatically by the controller 550.

In accordance with an embodiment of the present invention, after activation of the spray device 505 via actuator 560, the spray device 505 continues to spray the spray liquid until a single dosage of the spray liquid is dispensed and the removable liquid container 530 is substantially empty of the spray liquid. In accordance with another embodiment of the present invention, the spray of the spray liquid from the spray device 505, as well as the sweeping motion of the spray device 505, may be momentarily paused during the spray operation in order that the subject being sprayed can reposition themselves, or be automatically repositioned, with respect to the spray device 505. For example, during a single spraying operation, the spray of spray liquid from the spray device 505 may be paused one or more times, the subject may be instructed to turn his or her body in a new orientation, and then the spray of spray liquid from the spray device 505 may be resumed. Upon final completion of the spraying operation, the removable liquid container is substantially empty of the spray liquid. In accordance with still other embodiments of the present invention, deactivation of the spray device 505 may be performed either through the use of the actuator 560 or automatically by controller 550 after a predetermined time has elapsed, or based on a detected emptying of the removable liquid container.

Although the sweeping motion of the spray device 505 of FIG. 1 is illustrated as being primarily in a vertical direction, it should be understood that other embodiments of the present invention may be adapted to sweep the spray device 505 in a primarily horizontal direction. In still other embodiments of the spray device 505 of FIG. 1, the spray device 505 may be adapted to sweep using a combination of horizontal and vertical motions through the use of multi-axis pivot points.

In accordance with another embodiment of the present invention, the removable liquid container 530 may be adapted to hold a volume of spray liquid equal to that required to hold multiples of a single dosage of the spray liquid while still having a size small enough such that it may be easily installed and removed, as well as depleted before spoilage may occur. For example, in an application in which a typical single dosage of spray liquid is equal to approximately 100 ml to 150 ml, the removable liquid container 130 may be adapted to hold a volume of spray liquid of less than or equal to approximately one liter. At least one advantage provided by this embodiment is that multiple dosages can be dispensed from a single removable liquid container while still allowing the removable liquid container contents to be depleted before spoilage occurs.

Figure 2:
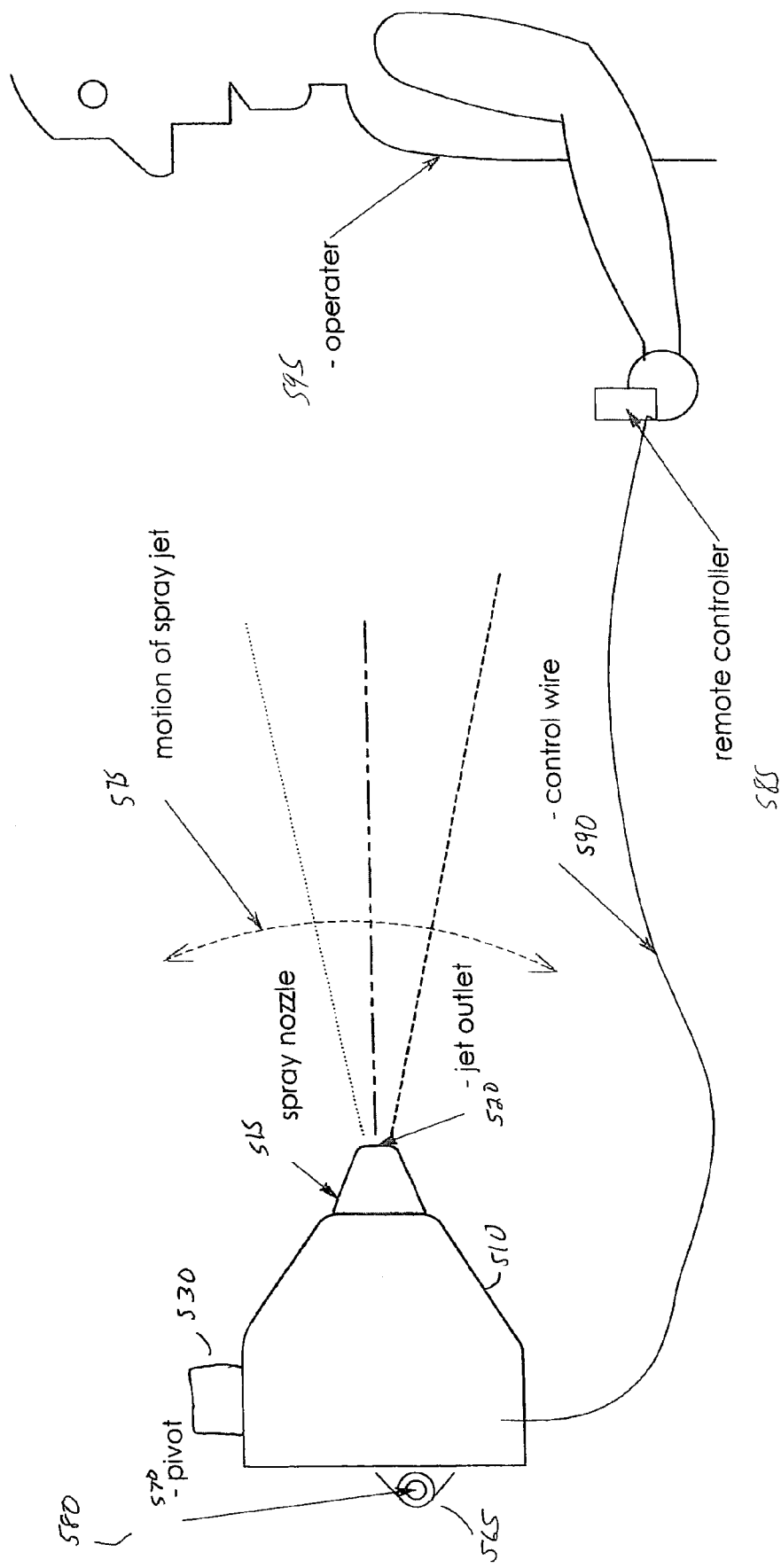
FIG. 2 illustrates an embodiment of the spray device of FIG. 1.

Referring now to FIG. 2, an embodiment of the spray device of FIG. 1 is illustrated. In the embodiment of FIG. 2, the actuator 560 of FIG. 1 is comprised of a remote controller 585 connected to the spray device 580 via a control wire 590. The remote controller 585 may be adapted to be of a size to be held in the hand. The remote controller 585 allows an operator 595 to remotely control operation of the spray device 580. In accordance with an embodiment of the present invention, the remote controller 585 allows an operator 595 or a person to be coated to control dispensing of spray liquid by the spray device 580. The remote controller 585 provides for remote activation of the spray device 580 by hand or foot while allowing the person to be coated to stand at an optimum distance away from the spray nozzle 515. The remote controller 585 may also allow, for example, for a person being coated to move body parts or completely turn in order to achieve uniform coverage while still retaining control over the spray device 580. In other embodiments of the present invention, the spray nozzle 515 may be comprised of an electrostatic spray nozzle. In such embodiments, the control wire 590 may be adapted to provide a connection to a ground for the operator 595.

In addition to starting and stopping the spray jet from the spray jet outlet 520, the remote controller 585 may be further adapted to control sweeping means 565 to oscillate the spray device 580 about pivot point 570. The remote controller 585 may allow an operator 595 to start and stop the sweeping motion 575 of the spray device 580, control the speed of the sweeping motion 575 of the spray device 580, and/or control the range of the sweeping motion 575 of the spray device 580. Stopping of the sweeping means 565 of the spray device 580 can be initiated through use of the remote controller 585 and/or automatically.

In accordance with still other embodiments of the present invention, it is not necessary to include a control wire 590 to connect the remote controller 585 to the spray device 580. Alternately, the remote controller 585 can be adapted to control the spray device 580 via a wireless connection, such as an infrared signal or other light signal, a radio signal, a motion signal, or a voice activation or other sound signal. In still other embodiments, the remote controller 585 may comprise a hydraulic flow device or a pneumatic flow device connected to the spray device 580 via a tube.

In accordance with an embodiment of the present invention, after activation of the spray device 580 via remote controller 585, the spray device 580 continues to spray the spray liquid until a single dosage of the spray liquid is dispensed and the removable liquid container 530 is substantially empty of the spray liquid. In accordance with another embodiment of the present invention, the spray of the spray liquid from the spray device 580, as well as the sweeping motion of the spray device 580, may be momentarily paused during the spray operation in order that the subject being sprayed can reposition themselves, or be automatically repositioned, with respect to the spray device 580. For example, during a single spraying operation, the spray of spray liquid from the spray device 580 may be paused one or more times, the subject may be instructed to turn his or her body in a new orientation, and then the spray of spray liquid from the spray device 580 may be resumed. Upon final completion of the spraying operation, the liquid container is substantially empty of the spray liquid. In accordance with still other embodiments of the present invention, deactivation of the spray device 580 may be performed either through the use of the remote controller 585 or automatically after a predetermined time has elapsed, or based upon a detected emptying of the liquid container.

Figure 3:
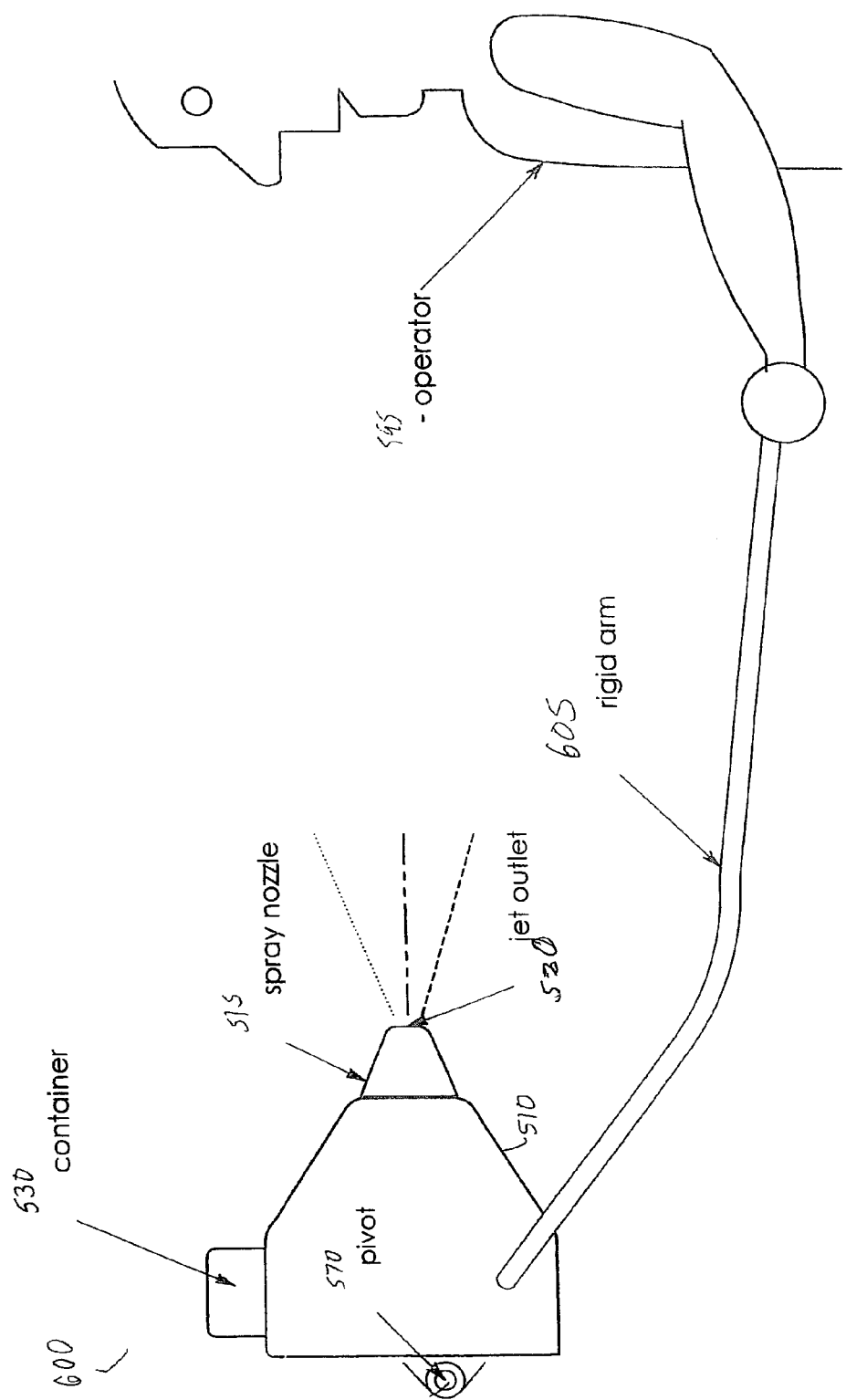
FIG. 3 illustrates a spray device in accordance with another embodiment of the present invention.

Referring now to FIG. 3, a spray device in accordance with another embodiment of the present invention is illustrated. The spray device 600 includes a manually-operated sweeping means 605 which allows an operator 595 to manually position the liquid spray from the jet outlet 520. In accordance with one embodiment of the present invention, the manually-operated sweeping means 605 may comprise a rigid arm, connected to the spray device 600, and adapted to be held in a hand of the operator 595, thus allowing a pivot action about pivot point 570 by movement of the rigid arm by the operator 595. In accordance with an embodiment of the present invention, the manually-operated sweeping means 605 allows manual positioning of the spray jet while the person being sprayed is at an optimal distance from the jet outlet 520. The manually-operated sweeping means 605 allows the spray jet to be positioned to spray certain parts of the body, or continuously oscillated to sweep the spray over larger areas or the entire body.

Although the sweeping motion of the spray device 600 of FIG. 3 is illustrated as primarily in a vertical direction, it should be understood that other embodiments of the present invention may be adapted to sweep the spray device 600 in a primarily horizontal direction. In still other embodiments of the spray device 600 of FIG. 3, the spray device 600 may be adapted to sweep using a combination of horizontal and vertical motions through the use of multi-axis pivot points. In still other embodiments of the spray device 600 of FIG. 3, the manually-operated sweeping means 605 may be provided with an actuator at the end of a handle, enabling the operator 595 to start and stop the spray during the treatment session.

Figure 4:
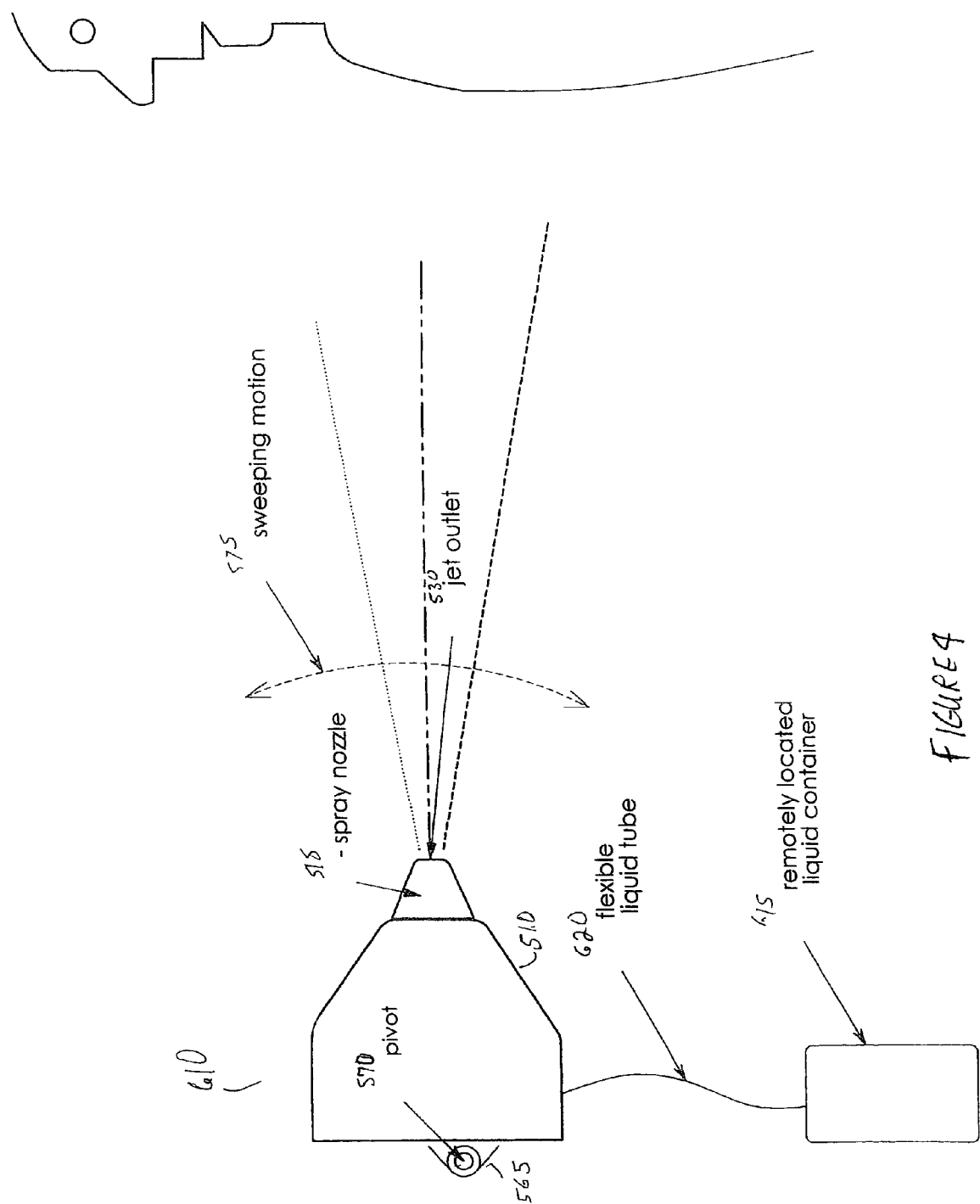
FIG. 4 illustrates a spray device in accordance with another embodiment of the present invention.

Referring now to FIG. 4, a spray device in accordance with another embodiment of the present invention is illustrated. The spray device 610 includes a remotely located liquid container 615 instead of the removable liquid container of the embodiments of FIGS. 1-3. The remotely located liquid container 615 is connected to the spray device 610 via a flexible liquid tube 620. In accordance with an embodiment of the present invention, the remotely located liquid container 615 is adapted to be of a size to contain an amount of liquid substantially equal to that required to apply a single dosage of the liquid to be sprayed to coat a surface of a human body. For example, this volume may be in the range of 100 ml to 150 ml. The amount of liquid substantially equal to that required to apply a single dosage may vary in accordance with the type of liquid and efficiency of the spray device, for example, between a range of 100 ml to 500 ml. In accordance with another embodiment of the present invention, the remotely located liquid container 615 may be adapted to hold a volume of spray liquid of less than one liter. In accordance with still another embodiment of the present invention, the remotely located liquid container 615 may comprise a disposable liquid container or a refillable liquid container. Although the present embodiment is described with reference to a single removable liquid container, it should be understood that a plurality of removable liquid containers may be used.

Figure 5:
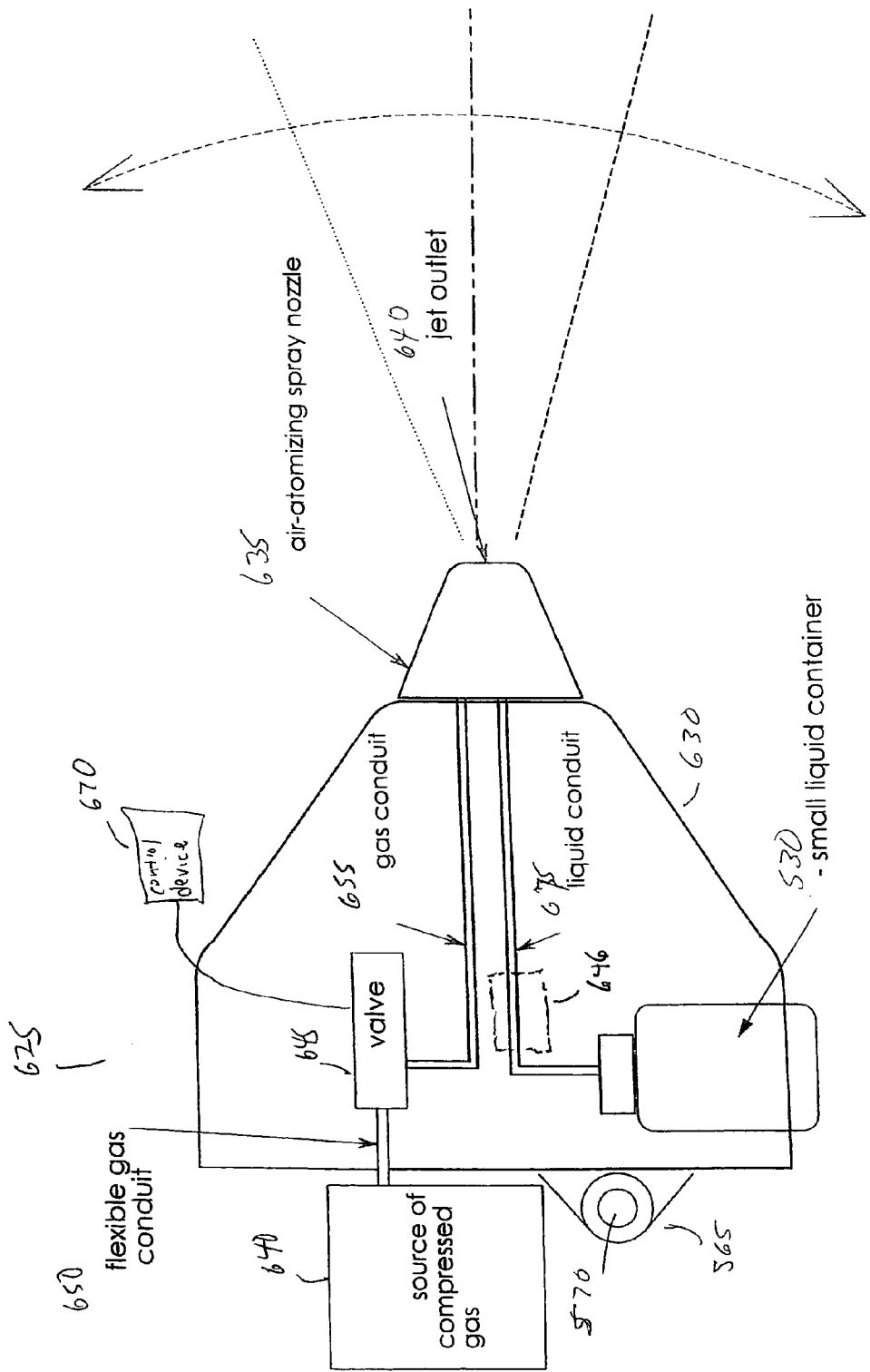
FIG. 5 illustrates an air-atomizing spray device adapted to coat a surface of a human body with a spray liquid in accordance with another embodiment of the present invention.

Referring now to FIG. 5, an air-atomizing spray device adapted to coat a surface of a human body with a spray liquid, such as a sunless tanning compound, in accordance with another embodiment of the present invention is illustrated. The spray device 625 includes a housing 630 having an attached air-atomizing spray nozzle 635. The air-atomizing spray nozzle 635 includes a jet outlet 640 for dispensing a spray of liquid to cover a portion of a human body. It should be understood that while the present embodiment is described as having a single air-atomizing spray nozzle 185, multiple spray nozzles may be used. In another embodiment of the present invention, the air-atomizing spray nozzle 635 may be comprised of an electrostatic spray nozzle adapted to produce electrostatically charged droplets of the spray liquid.

The housing 630 is adapted to receive and support an inserted removable liquid container 530. In accordance with an embodiment of the present invention, the removable liquid container 530 is adapted to be of a size to contain an amount of liquid substantially equal to that required to apply a single dosage of the liquid to be sprayed to coat a surface of a human body. For example, this volume may be in the range of 100 ml to 150 ml. The amount of liquid substantially equal to that required to apply a single dosage may vary in accordance with the type of liquid and efficiency of the spray device, for example, between a range of 100 ml to 500 ml. In accordance with still another embodiment of the present invention, the removable liquid container 530 may comprise a disposable liquid container or a refillable liquid container. Although the present embodiment is described with reference to a single removable liquid container, it should be understood that a plurality of removable liquid containers may be used.

Upon insertion of the removable liquid container 530 into the housing 630, a liquid conduit 675, or liquid channel, connects the removable liquid container 530 to the air-atomizing spray nozzle 635. The spray device 625 is further adapted to support the connection of a source of compressed gas 640 to a gas valve 645 via a flexible gas conduit 650. The gas valve 645 is further connected to the air-atomizing spray nozzle 635 via a gas conduit 655. A control device 670 is connected to the gas valve 645 to control operation of the gas valve 645.

Upon opening of the gas valve 645, gas from the source of compressed gas 640 is allowed to flow to air-atomizing nozzle 635. Through a Venturi action of the gas flowing to the air-atomizing nozzle 635, liquid in the removable liquid container 530 is pulled through the liquid conduit 675 to the air-atomizing spray nozzle 635, and exits the air-atomizing spray nozzle 635 through jet outlet 640 in the form of an air-atomized liquid spray. The removable liquid container 530 may optionally be pressurized or vented to facilitate the dispensing of liquid from the liquid container 530. In an alternate embodiment of the present invention, a liquid valve 646 may additionally be used to control flow of liquid in the liquid conduit 675 from removable liquid container 530, although it is not required.

In accordance with an embodiment of the present embodiment, the control device 670 may comprise a remote control, an actuator, a timer, or a programmable controller. In accordance with various embodiments, the control device 670 may be adapted to be a hand-held actuator or remote control, mounted on the housing 630 of the spray device 625, or mounted on a wall or a floor near the person to be coated by the liquid spray, thereby providing remote activation of the spray device 625 by hand or foot while allowing a person to be coated to stand at an optimum distance away from the air-atomizing spray nozzle 635. The remote activation provided by the control device 670 allows, for example, for the person being coated to move body parts or completely turn in order to achieve uniform coverage. It should be understood that activation of the spray device 625 may be controlled either by an operator or the person to be coated. In accordance with still other embodiments of the present invention, the control device 625 may be adapted to control the gas valve 645 via a wireless connection, such as an infrared or other light signal, a radio signal, a motion signal or a voice activation or another sound signal. In still other embodiments, the control device 670 may comprise a hydraulic flow device or a pneumatic flow device connected to the spray device 625 via a tube. In still another embodiment of the present invention, the gas valve 645 may be comprised of a mechanical toggle valve with the toggle valve and associated conduits positioned outside of the housing 630 and held as a hand-held remote control, or positioned in a location convenient to the operator, such as mounted on a wall or floor.

In accordance with the present embodiment, the spray device 625 further includes a sweeping means 565 that is adapted to oscillate the spray device 625 about a pivot point 570 in a sweeping motion, such as in a predetermined arc, while spraying. The sweeping motion imparted to the air-atomizing spray nozzle 635 provides for the liquid spray from the jet outlet 640 to provide a larger area of coverage than that provided by a stationary nozzle. The sweeping means of the present embodiment can be comprised of any of the sweeping means previously described. The sweeping means 565 may be comprised of, for example, an oscillating motor, one or more solenoids, or hydraulic actuators. The flexible gas conduit 650 allows the source of compressed gas 640 to remain fixed while the spray device 625 is moved in a sweeping motion.

In accordance with an embodiment of the spray device 625, the control device 670 is further adapted to control the sweeping motion of the spray device 625. For example, in addition to starting and stopping the spray jet from the spray jet outlet 640, the control device 670 may be used to start and stop the sweeping movement, control the speed of the sweeping movement, and/or control the range of the sweeping movement of the spray device 625. Activation of the control device 670 to start the sweeping movement of the spray device 625 can be initiated through use of the of an actuator and/or automatically by the control device 670. Similarly, stopping of the sweeping movement of the spray device 625 can be initiated through use of an actuator and/or automatically by the control device 670.

In accordance with an embodiment of the present invention, after activation of the spray device 625 via control device 670, the spray device 625 continues to spray the spray liquid until a single dosage of the spray liquid is dispensed and the removable liquid container 530 is substantially empty of the spray liquid. In accordance with another embodiment of the present invention, the spray of the spray liquid from the spray device 625, as well as the sweeping motion of the spray device 625, may be momentarily paused during the spray operation in order that the subject being sprayed can reposition themselves, or be automatically repositioned, with respect to the spray device 625. For example, during a single spraying operation, the spray of spray liquid from the spray device 625 may be paused one or more times, the subject may be instructed to turn his or her body in a new orientation, and then the spray of spray liquid from the spray device 625 may be resumed. Upon final completion of the spraying operation, the removable liquid container is substantially empty of the spray liquid. In accordance with still other embodiments of the present invention, deactivation of the spray device 625 may be performed either through the use of the control device 670, automatically after a predetermined time has elapsed, or based on a detected emptying of the liquid container.

Although the sweeping motion of the spray device 625 of FIG. 5 is illustrated as primarily in a vertical direction, it should be understood that other embodiments of the present invention may be adapted to sweep the spray device 625 in a primarily horizontal direction. In still other embodiments of the spray device 625 of FIG. 5, the spray device 625 may be adapted to sweep using a combination of horizontal and vertical motions through the use of multi-axis pivot points.

Figure 6:
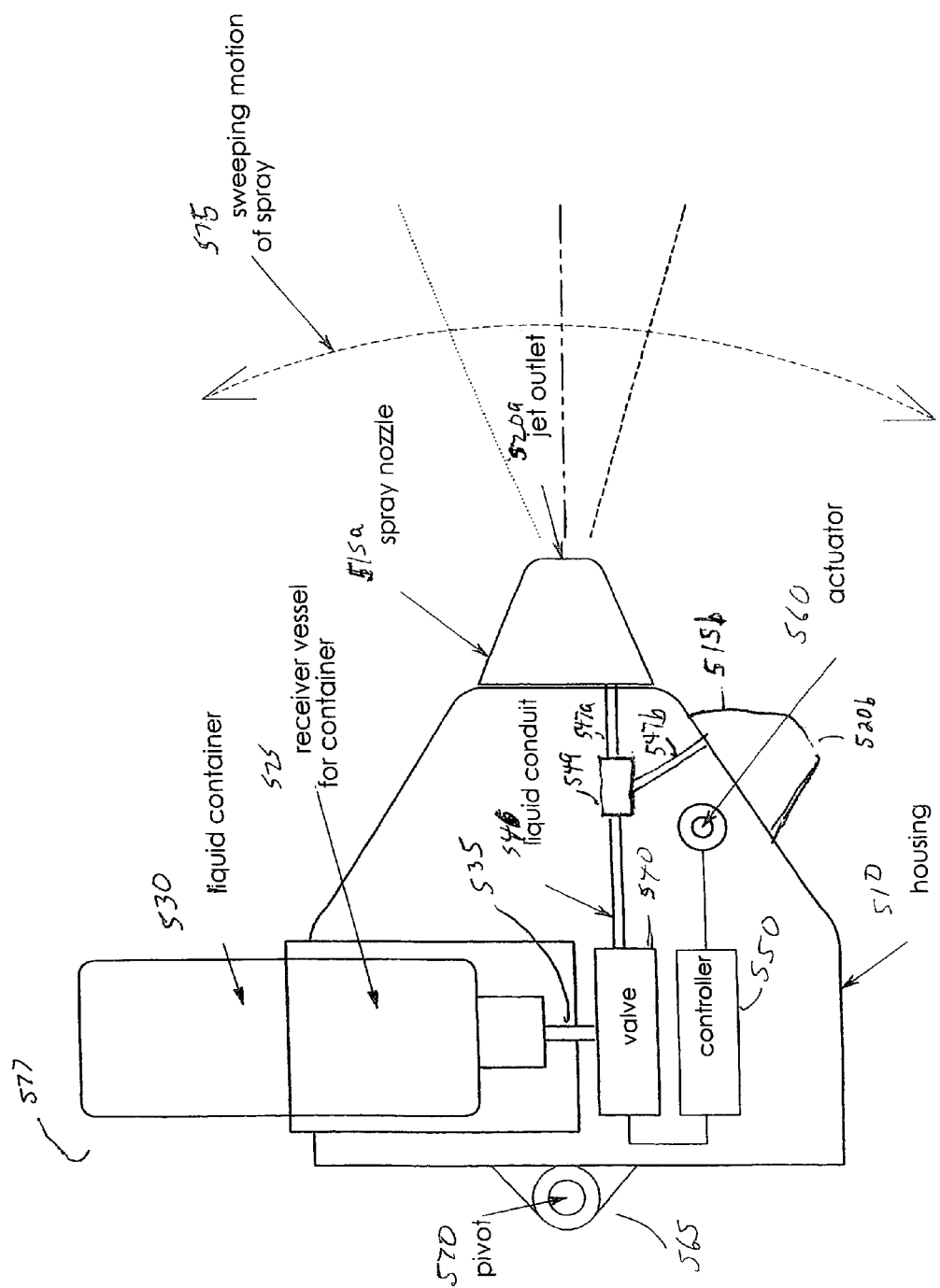
FIG. 6 illustrates a multi-nozzle spray device adapted to coat a surface of a human body with a spray liquid in accordance with another embodiment of the present invention.

Referring now to FIG. 6, a multi-nozzle spray device adapted to coat a surface of a human body with a spray liquid, such as a sunless tanning compound, in accordance with another embodiment of the present invention is illustrated. The spray device 577 includes a housing 510, a receiver vessel 525, a removable liquid container 530, a receiver conduit 535, a liquid valve 540, a controller 550, an actuator 560, a sweeping means 565, and a pivot point 570 similar to or the same as those described in relation to FIG. 1. No further description of these components is provided except when necessary.

The spray device 577 further includes a liquid conduit 546 connecting the liquid valve 540 to a metering device 549. The spray device 577 further includes a first nozzle conduit 547a connecting the metering device 549 to a first spray nozzle 515a having a first jet outlet 520a, and a second nozzle conduit 547b connecting the metering device 549 to a second spray nozzle 515b having a second jet outlet 520b. The metering device 549 is adapted to control the flow of fluid through the first nozzle conduit 547a and the second nozzle conduit 547b. In accordance with an embodiment of the present invention, the metering device 549 is adapted to control the flow of fluid such that equal volumes of spray liquid are provided to each of the first spray nozzle 515a and the second spray nozzle 515b during the spraying operation. In accordance with another embodiment of the present invention, the metering device 549 may be adapted to provide a different measured volume of liquid to each of the first spray nozzle 515a and the second spray nozzle 515b. In accordance with an embodiment of the present invention, the metering device 549 can be comprised of a solenoid, pump, or any other suitable liquid metering device. In accordance with still another embodiment of the present invention, separate metering devices may be provided in each of the spray nozzles. Although the present embodiment is illustrated using two spray nozzles, it should be understood that any number of a plurality of liquid nozzles may be used.

In an embodiment of the present invention, the liquid conduit 546, the first nozzle conduit 547a, and the second nozzle conduit 547b are all adapted to be of a length such that the distance that the liquid is required to flow between the liquid valve 540 and the first spray nozzle 515a and the second spray nozzle 515b is short enough that purging of the spray device 577 is not necessary between applications.

Figure 7:
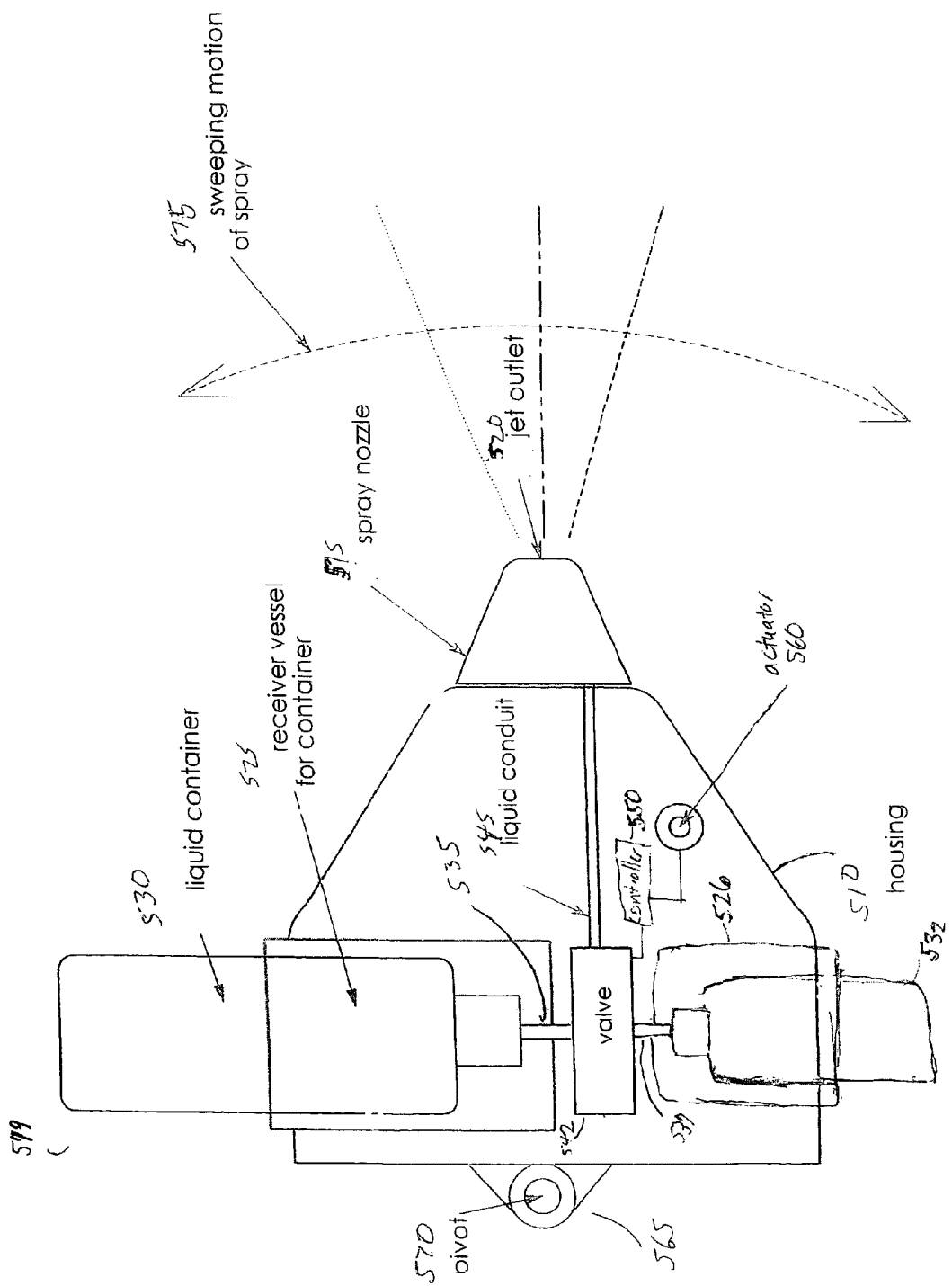
FIG. 7 illustrates a multi-receiver vessel spray device adapted to coat a surface of a human body with a spray liquid in accordance with another embodiment of the present invention.

Referring now to FIG. 7, a multi-receiver vessel spray device adapted to coat a surface of a human body with a spray liquid, such as a sunless tanning compound, in accordance with another embodiment of the present invention is illustrated. In accordance with the present embodiment, the spray device 579 includes a housing 510, a spray nozzle 515, a jet outlet 520, a receiver vessel 525, a removable liquid container 530, a receiver conduit 535, a liquid conduit 545, a controller 550, an actuator 560, a sweeping means 565, and a pivot point 570 similar to or the same as those described in relation to FIG. 1. No further description of these components is provided except when necessary. The receiver conduit 535 is further connected to a liquid valve 542.

The spray device 579 further includes another receiver vessel 526 adapted to receive and support another removable liquid container 532. In accordance with an embodiment of the present invention, the removable liquid container 532 is adapted to be disposable after use. In accordance with one embodiment of the present invention, the receiver vessel 526 may be of a shape so that it mates with the outside shape of the removable liquid container 532 to properly orient the removable liquid container 532 within the receiver vessel 526, as well as ensure that the correct container is used in the spray device 579. Upon insertion of the removable liquid container 532 into the receiver vessel 526, a receiver conduit 137 connected to the liquid valve 542 punctures a liquid seal in the removable liquid container 532. In accordance with an embodiment of the present invention, the removable liquid container 532 is adapted to be of a size to contain an amount of liquid substantially equal to that required to apply a single dosage of the liquid to be sprayed to coat a surface of a human body. For example, this volume may be in the range of 100 ml to 150 ml. The amount of liquid substantially equal to that required to apply a single dosage may vary in accordance with the type of liquid and efficiency of the spray device, for example, between a range of 100 ml to 500 ml.

In accordance with the embodiment of FIG. 7, the liquid valve 542 is adapted to selectively allow the flow of spray liquid from one of the removable liquid container 530 and the removable liquid container 532 through the liquid conduit 545 to the spray nozzle 515, and exit the spray nozzle 515 through jet outlet 520 in the form of a liquid spray. In accordance with one embodiment of the present invention, the selection of which one of the spray liquids from removable liquid container 530 and the removable liquid container 532 that is allowed by the liquid valve 542 to flow to the spray nozzle 515 may be performed by an operator using the actuator 560.

The embodiment of FIG. 7 provides for the use of multiple removable liquid containers in a single tanning session. In accordance with one embodiment, the contents of each of the removable liquid containers may be applied sequentially. For example, a particular customer may desire to have a pre-tanning compound from a first removable liquid container be applied, and then subsequently have a tanning compound from a second removable liquid container be applied. Switching between the first removable liquid container and the second removable liquid container may be performed through the use of the actuator 560 or automatically after a predetermined time has elapsed, or based on a detected emptying of the removable liquid container. In accordance with still another embodiment of the present invention, the liquid valve 542 may adapted to allow the flow of spray liquid from the first removable liquid container and the second removable liquid container simultaneously, thus allowing for mixing of the solutions during application. Although the present embodiment is illustrated using two removable liquid containers, it should be understood that any number of a plurality of removable liquid containers may be used.

Figure 8:
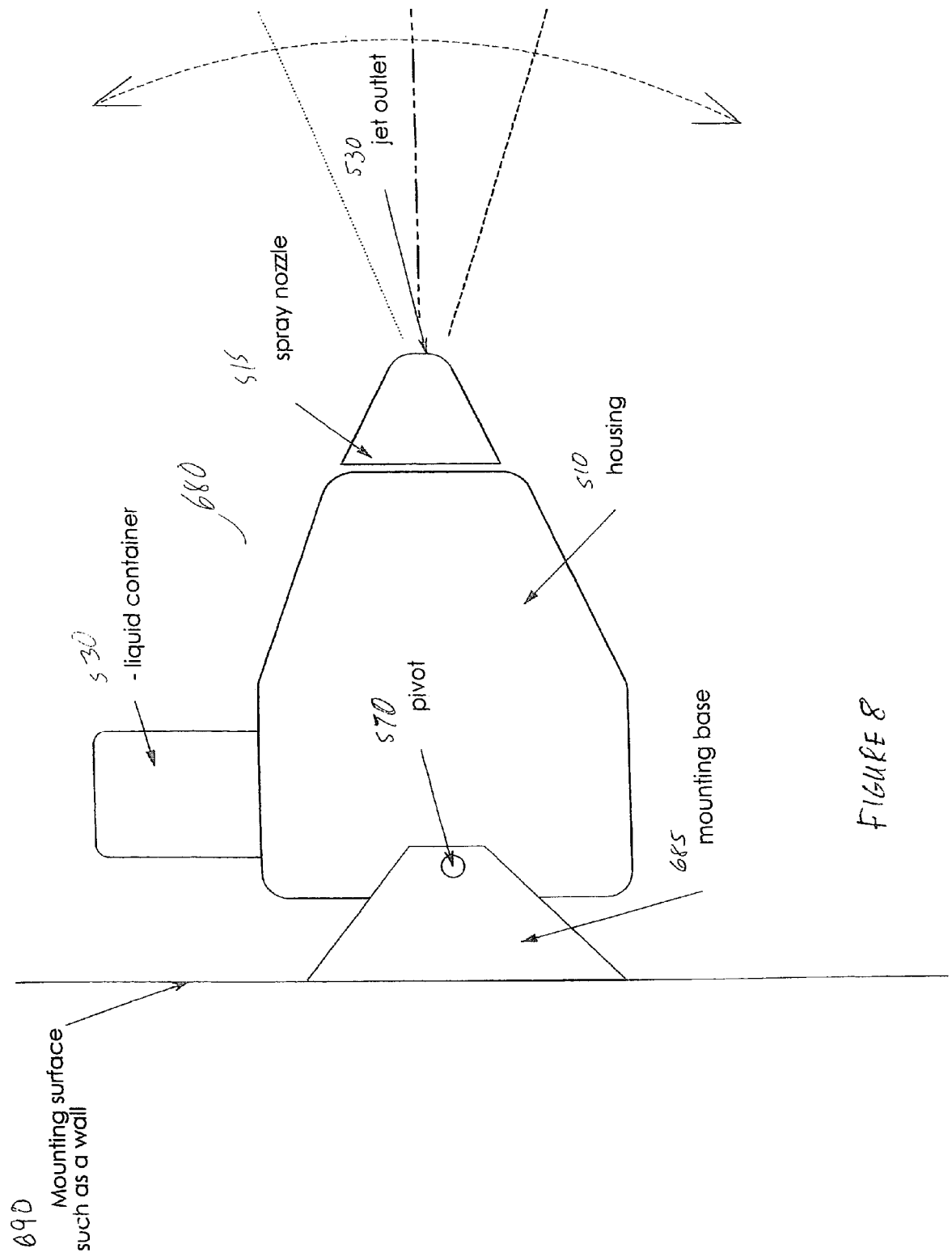
FIG. 8 illustrates an embodiment of a mounting arrangement for use with at least one embodiment of the spray device of the present invention.

Referring now to FIG. 8, an embodiment of a mounting arrangement for use with at least one embodiment of a spray device of the present invention is illustrated. The spray device 680, which may be comprised of any of embodiments of the spray devices as described in FIGS. 1-7, is adapted to be mounted to a mounting base 685 via a pivot point 570. The mounting base 685 is adapted to be mounted on a vertical mounting surface 690, such as a wall or a pole stand. The pivot point 570 is adapted to act as a swivel point to allow the sweeping means (not shown) to oscillate the spray device 680 in a sweeping motion. It should be understood that other means for mounting the various embodiment of the spray device of the present invention may be used, such as a gantry system.

Referring now to FIG. 9, another embodiment of a mounting arrangement for use with at least one embodiment of a spray device of the present invention is illustrated. The spray device 695, which may be comprised of any of the embodiments of the spray devices as described in reference to FIGS. 1-7, is adapted to be mounted to a mounting base 700 via a pivot point 570. The mounting base 700 is adapted to be mounted on a horizontal mounting surface 705, such as a table top, counter, or stand. The pivot point 570 is adapted to act as a swivel point to allow the sweeping means (not shown) to oscillate the spray device 680 in a sweeping motion. It should be understood that other means for mounting the various embodiment of the spray device of the present invention may be used, such as using a gantry system.

Several advantages are provided by various embodiment of the spray device of the present invention. For example, in a self-tanning application, the use of small, individual liquid containers rather than bulk tanks allows for a customer to choose from among a variety of self-tanning solutions. In addition, it allows for the customer to choose from a variety of pre-treatment and post-treatment lotions that improve the tanning process, such as lotions, dehydrants, accelerators, and fragrances to mask the DHA chemical odor present in certain self-tanning solutions. The use of small individual liquid containers of various volumes, allows the liquid volume of a single application to be readily adjusted to match a particular individual body size.

Another advantage provided by embodiments of the present invention is that the risk of a poor tanning result is reduced since the usage of a single application liquid container prevents the rapid spoilage which occurs in larger tanks of sunless tanning compounds after they are opened. An additional advantage that may be provided is that the customer may be ensured of a fresh solution of sunless tanning compound for each tanning experience. A further advantage is that may be provided is that the customer and salon personnel are reassured that the correct dosage is being applied by the spray device during each tanning session.

A further advantage that may be provided by embodiments of the present invention is that the need for maintenance be reduced, and safety and convenience can be improved for salon personnel since large tanks do not have to be moved or poured. Another advantage provided by various embodiment of the present invention is that overall system reliability is improved by eliminating the use of long hoses from tanks to nozzles. In addition, the close proximity of the removable liquid container to the nozzle allows the use of shorter hoses which reduces or eliminates the need for purging the hoses when changing containers, thus enabling the spray device to be self-cleaning. Still another advantage that may be provided by embodiments of the present invention is that it allows application to selected body parts, for example, application to the face or legs.

A further advantage that may be provided by embodiments of the present invention is allows a spray device to be imparted with a sweeping motion to optimize spray coverage and convenience for a customer.

Although a preferred embodiment of the method and apparatus of the present invention has been illustrated in the accompanying Drawings and described in the foregoing Detailed Description, it is understood that the invention is not limited to the embodiment disclosed, but is capable of numerous rearrangements, modifications, and substitutions without departing from the spirit of the invention as set forth and defined by the claims.

What is claimed:

1. A spray device comprising:
    a housing including:
        at least one nozzle mounted to the housing for spraying a user;
        a receiver configured to allow the housing to receive at least one user-insertable/removable single-use liquid container; and
        a liquid channel within the housing connecting the received at least one single-use liquid container to the at least one nozzle;
    a spray valve controlling spraying of a spray liquid from the received at least one single-use liquid container by the at least one nozzle onto the user the at least one nozzle producing a spray jet of the spray liquid; and
    a pivoting sweeping means coupling the housing to a mounting surface, the pivoting sweeping means for allowing movement of the housing so as to sweep the spray jet from the at least one nozzle to coat at least a portion of the user.

2. The spray device of claim 1, wherein the at least one single-use liquid container comprises a disposable liquid container.

3. The spray device of claim 1, wherein the at least one single-use liquid container comprises a refillable liquid container.

4. The spray device of claim 1, wherein the spray liquid comprises a sunless tanning compound.

5. The spray device of claim 1, wherein the pivoting sweeping means is adapted to allow an oscillating motion of the housing.

6. The spray device of claim 1, wherein the pivoting sweeping means allows a substantially vertical movement of the housing.

7. The spray device of claim 1, wherein the pivoting sweeping means allows a substantially horizontal movement of the housing.

8. The spray device of claim 1, wherein the pivoting sweeping means allows a horizontal movement and a vertical movement of the housing.

9. The spray device of claim 1, wherein the pivoting sweeping means comprises an automatic sweeping means.

10. The spray device of claim 1, wherein the pivoting sweeping means comprises a manually-operated sweeping means.

11. The spray device of claim 10, wherein the manually-operated sweeping means comprises a manually-operated lever.

12. The spray device of claim 1, further comprising a control device adapted to control the operation of the pivoting sweeping means.

13. The spray device of claim 12, wherein the control device is further adapted to control a speed of movement of the pivoting sweeping means.

14. The spray device of claim 12, wherein the control device comprises a remote control.

15. The spray device of claim 14, wherein the remote control is connected to the spray device by a wire.

16. The spray device of claim 12, wherein the control device is adapted to control the operation of the spray valve via at least one of a light signal, a radio signal, a motion signal, and a sound signal.

17. The spray device of claim 12, wherein the control device comprises an automatic control device.

18. The spray device of claim 17, wherein the automatic control device comprises at least one of a timer and a programmable controller.

19. The spray device of claim 17, wherein operation of the automatic control device is initiated by an electrical switch.

20. The spray device of claim 12, wherein the control device is further adapted to electrically connect an operator of the control device to a ground.

21. The spray device of claim 1, wherein the mounting surface comprises a horizontal surface.

22. The spray device of claim 1, wherein the mounting surface comprises a vertical surface.

23. The spray device of claim 1, wherein the mounting surface comprises a gantry system.

24. The spray device of claim 1, wherein the at least one nozzle comprises a plurality of nozzles, and the spray device further comprises a metering device adapted to control the flow of spray liquid through the plurality of nozzles.

25. A spray device for coating the surface of a user's human body with a spray liquid, the spray device comprising:
    a housing having a pivot attachment mechanism to allow movement of the housing to sweep a spray jet to coat at least a portion of the user's human body, the housing including:
        at least one nozzle mounted to the housing to spray the user;
        a receiver vessel for receiving within the housing a first end of at least one user-insertable/removable single-use liquid container; and
        a liquid channel connecting the received at least one liquid container to the at least one nozzle;
    a spray valve controlling spraying of a spray liquid from the received at least one single-use liquid container by the at least one nozzle, the at least one nozzle producing a spray liquid; and
    a control device which controls operation of the spray device to perform a single spraying operation onto the user at the completion of which the received single-use liquid container is substantially empty.

26. The spray device of claim 25, wherein the at least one single-use liquid container holds a volume of spray liquid substantially equal to that required to apply a predetermined multiple of a single application of the spray liquid to the surface of the user's human body.

27. The spray device of claim 25, wherein the spray liquid comprises a sunless tanning compound.

28. The spray device of claim 25, wherein the pivot attachment mechanism supports an oscillating motion of the spray jet.

29. The spray device of claim 25, wherein the pivot attachment mechanism comprises an automatic sweeping means.

30. The spray device of claim 25, wherein the pivot attachment mechanism comprises a manually-operated pivot attachment mechanism.

31. The spray device of claim 25, wherein the control device is further adapted to control operation of the pivot attachment mechanism.

32. The spray device of claim 25, further comprising a mount for mounting the spray device to a surface.

33. The spray device of claim 1, wherein the at least one single-use liquid container holds a maximum volume of spray liquid not to exceed that which is substantially equal to an amount required to apply a single dosage of the spray liquid in a single spray session for coating a surface of the user's body.

34. The spray device of claim 1, wherein the at least one single-use liquid container holds a maximum volume of spray liquid in the range of 100 milliliters to 500 milliliters.

35. The spray device of claim 1, wherein the at least one single-use liquid container holds a maximum volume of spray liquid in the range of 100 to 150 milliliters.

36. The spray device of claim 1, wherein the at least one single-use liquid container holds a maximum volume of spray liquid of less than one liter.

37. The spray device of claim 1, further comprising:
    a pressurized gas conduit, the pressurized gas conduit connecting a source of compressed gas to the at least one nozzle, wherein the flow of pressurized gas to the at least one nozzle facilitates flow of the spray liquid from the at least one single-use liquid container to the at least one nozzle using the liquid channel.

38. A spray device comprising:
    a housing including:
        at least one nozzle mounted to the housing;
        a receiver vessel for receiving through an opening in the housing a first end of at least one insertable/removable single-use liquid container, the received at least one single-use liquid container holding a maximum volume of spray liquid not to exceed that which is substantially equal to an amount required to apply a single dosage of the spray liquid in a single operation session for coating a surface of a human body; and
        a liquid channel connecting the received at least one single-use liquid container to the at least one nozzle;
    a spray valve controlling the spraying of the spray liquid from the received at least one single-use liquid container by the at least one nozzle, the at least one nozzle producing a spray jet of the spray liquid; and
    a pivot attachment mechanism coupled to the housing, the pivot attachment mechanism allowing movement of the housing to sweep the spray jet from the at least one nozzle to coat at least a portion of the human body.

39. The spray device of claim 38, wherein the pivot attachment mechanism is adapted to allow an oscillating motion of the spray jet.

40. The spray device of claim 38, wherein the pivot attachment mechanism comprises an automatic sweeping means.

41. The spray device of claim 38, wherein the sweeping means comprises a manually-operated sweeping means.

42. The spray device of claim 38, further comprising a control device adapted to control operation of the pivot attachment mechanism.

43. A spray device for coating a surface of a human body with a spray liquid, the spray device comprising:
    a housing including:
        at least one nozzle mounted to the housing for spraying a user;
        a receiver vessel for receiving within the housing a first end of at least one user-insertable/removable single-use liquid container, the first end of the received at least one single-use liquid container having an open end closed by a liquid seal;
        a receiver conduit placed within the receiver vessel to puncture the liquid seal of the received at least one single-use liquid container; and
        a liquid channel connecting the received at least one single-use liquid container to the at least one nozzle; and
    a pivoting sweeping means coupled to the housing, the pivoting sweeping means for allowing movement of the housing to sweep a liquid spray jet from the at least one nozzle to coat at least a portion of a human body.

44. The spray device of claim 43, wherein the pivoting sweeping means is adapted to allow an oscillating motion of the spray jet.

45. The spray device of claim 43, wherein the pivoting sweeping means comprises an automatic sweeping means.

46. The spray device of claim 43, wherein the pivoting sweeping means comprises a manually-operated sweeping means.

47. The spray device of claim 43, further comprising a control device adapted to control operation of the sweeping means.

48. A spray device comprising:
a housing including:
at least one nozzle mounted to the housing;
a receiver vessel for receiving within the housing an open end of at least one insertable/removable single-use liquid container closed by a liquid seal, the at least one single-use liquid container holding a maximum volume of spray liquid not to exceed that which is substantially equal to an amount required to apply a single dosage of the spray liquid in a single spray session for coating a surface of a human body;
a receiver conduit placed within the receiver vessel to puncture the liquid seal of the received at least one single-use liquid container; and
a liquid channel connecting the received single-use liquid container the at least one nozzle; and
a pivoting sweeping means coupled to the housing, the pivoting sweeping means allowing for movement of the housing to sweep a spray jet from the at least one nozzle to coat at least a portion of a human body.

49. The spray device of claim 48, wherein the pivoting sweeping means is adapted to allow an oscillating motion of the spray jet.

50. The spray device of claim 48, wherein the pivoting sweeping means comprises an automatic sweeping means.

51. The spray device of claim 48, wherein the pivoting sweeping means comprises a manually-operated sweeping means.

52. A spray device comprising:
a housing including:
at least one nozzle mounted to the housing for spraying a user;
a receiver adapted to receive within the housing a first end of at least one user insertable/removable single-use liquid container, wherein a second end of the single-use liquid container extends outside the housing after insertion by the user and reception by the receiver; and
a liquid channel connecting the received at least one single-use liquid container to the at least one nozzle;
a spray valve controlling spraying of the spray liquid from the received at least one single-use liquid container to the at least one nozzle, the at least one nozzle producing a spray jet of the spray liquid for application onto the user; and
an attachment mechanism for mounting the housing to a fixed surface, wherein the attachment mechanism is configured to allow the housing to move with respect to the fixed surface.

53. The spray device of claim 52, wherein the fixed surface is a vertical surface.

54. The spray device of claim 52, wherein the fixed surface is a horizontal surface.

55. The spray device of claim 52, wherein the movement of the housing with respect to the fixed surface is a sweeping movement.

56. The spray device of claim 52, wherein the movement of the housing with respect to the fixed surface is an oscillatory movement.

57. The spray device of claim 52, wherein the movement of the housing with respect to the fixed surface is a vertical movement.

58. The spray device of claim 52, wherein the movement of the housing with respect to the fixed surface is a horizontal movement.

59. The spray device of claim 52, wherein the movement of the housing with respect to the fixed surface is a horizontal movement and a vertical movement.

60. The spray device of claim 52, wherein the movement of the housing with respect to the fixed surface is a pivotal movement.

* * * * *

UNITED STATES PATENT AND TRADEMARK OFFICE
CERTIFICATE OF CORRECTION

| | | |
|---|---|---|
| PATENT NO. | : 7,297,211 B2 | Page 1 of 1 |
| APPLICATION NO. | : 10/841734 | |
| DATED | : November 20, 2007 | |
| INVENTOR(S) | : Steven C. Cooper et al. | |

It is certified that error appears in the above-identified patent and that said Letters Patent is hereby corrected as shown below:

In the Claims:

At column 16, claim number 38, line number 27, please replace the word [operation] with the word -- operating --.

Signed and Sealed this

Thirtieth Day of August, 2011

David J. Kappos
*Director of the United States Patent and Trademark Office*